US00PP14782P2

(12) United States Plant Patent
Stemkens

(10) Patent No.: US PP14,782 P2
(45) Date of Patent: May 11, 2004

(54) DIASCIA PLANT NAMED 'DIASTARA'

(50) Latin Name: *Diascia barberae*
Varietal Denomination: Diastara

(75) Inventor: Henricus G. W. Stemkens, Hoorn (NL)

(73) Assignee: Syngenta Seeds BV, Enkhuizen (NL)

( * ) Notice: Subject to any disclaimer, the term of this patent is extended or adjusted under 35 U.S.C. 154(b) by 0 days.

(21) Appl. No.: 10/340,261

(22) Filed: Jan. 10, 2003

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Bruce Vrana; Edouard G. Lebel

(57) ABSTRACT

A new Diascia plant particularly distinguished by its large blush flowers combined with deeprose spurs, early flowering and a habit that is first erect and later spreading.

1 Drawing Sheet

Varietal denomination: 'Diastara'.

BACKGROUND OF THE NEW PLANT

The present invention comprises a new distinct cultivar of Diascia, botanically known as *Diascia barberae*.

The new cultivar is propagated from cuttings resulting from the cross of 'B8' and 'B6'. 'B8' is a white flowering Diascia having a spreading habit and large flowers. 'B8' is not commercially available and is not known by any synonyms. 'B6' is a coral flowering Diascia having a spreading habit and intermediate flowers. 'B6' is not commercially available and is not known by any synonyms. Neither 'B8' nor 'B6' has been patented.

As a result of this cross the present cultivar was created in 1999 in Enkhuizen, Netherlands and has been repeatedly asexually reproduced by cuttings in Enkhuizen, Netherlands and Sarrians, France over a three-year period. It has been found to retain its distinctive characteristics through successive propagations, and this novelty appears to be firmly fixed.

This new Diascia plant is an annual in most climatical zones in the United States, only in zones 7, 8, 9 and 10 it is a perennial plant.

DESCRIPTION OF THE DRAWING

This new Diascia plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Diascia. The data which defines these characteristics were collected from asexual reproductions carried out in Enkhuizen, Netherlands. The plant history was taken on 10 weeks old plants, blossomed under natural light in a greenhouse.

Color readings were taken in the greenhouse under ambient light. Color references are primarily to The R.H.S. Colour Chart of The Royal Horticultural Society of London.

TABLE 1

Differences between the new cultivar 'Diastara', its parents and a similar cultivar

| | 'Diastara' | 'B8' | 'B6' | 'Pentiier' |
|---|---|---|---|---|
| Flower color | Blush | White | Coral | Light blush |
| Spur color | Deep rose | White | Purple-red | Pink |
| Leaf color | Deep green | Light green | Green | Green |

The plant:

*Classification.*—Botanical: *Diascia barberae.*

*Parentage.*—Female parent: A seedling named 'B8' is one of our seedlings from our B-generation of plants bred in 1997. Pollen parent: A seedling named 'B6' is one of our seedlings from our B-generation of plants bred in 1997.

*Growth habit.*—Semi-correct, spreading.

*Plant height.*—23–28 cm.

*Speading area of plant.*—20–26 cm.

*Growth rate.*—Vigorous.

*Strength.*—Very good.

*Branching character.*—Freely branching and lateral branching at every node.

*Quantity of branches.*—80–110 branches per plant.

*Blooming period.*—From April until November.

The stem:

*Diameter.*—0.5–1.0 mm.

*Shape.*—Round.

*Color.*—141A.

*Anthocyan pigmentation.*—Absent.

*Length of internode.*—Vegetative growth: 10–30 mm. Generative growth: 15–40 mm.

*Pubescence.*—Not pubescent.

The foliage:

*Phyllotaxis.*—Opposite.

*Shape of blade.*—Cordate to ovate.

*Texture.*—Upper side: Smooth. Lower side: Smooth.

*Attachment to leaf.*—Petiolate.

*Venation.*—Pinnate.

*Leaf margin.*—Serrate.

*Leaf base.*—Subcordate.

*Leaf apex.*—Acute.

*Length.*—14–20 mm.
*Width.*—12–18 mm.
*Depth of incision.*—1 mm.
*Color.*—Upper side: 137B. Lower side: 141C.
*Pubescence.*—No pubescence.
*Length of petiole.*—2–3 mm.
*Color of petiole.*—141C.
*Petiole surface texture.*—Smooth.

The bud:
*Peduncle length.*—20–40 mm, depending on season.
*Peduncle shape.*—Long and threadlike.
*Size of the bud.*—Length: 3 mm. Diameter: 3 mm.
*Shape.*—Oval.
*Color.*—141B.
*Sepals.*—Color: 141B. Form: Star-shaped. Number: 5, parted. Size: 1–2 mm. Shape: Elliptic, apex acute. Margin: Entire. Texture: Smooth.

The flower:
*Flower width.*—14–18 mm.
*Flower length.*—16–20 mm.
*Flower depth.*—8–10 mm.
*Flower aspect.*—Tipped upward and outward.
*Borne.*—Solitary.
*Form.*—Zygomorphic, five lobed, double nectar spur.
*Cluster.*—Raceme.
*Color.*—Upper surface: Going from 69D on the edge to 65A in the center. Lower surface: Going from 69C on the edge to 63B near the spur.
*Overlapping of the petals.*—Separate.
*Number of petals.*—Five.
*Shape of the petals.*—Two upper banner petals, two lateral petals and one larger basal lip petal. Base of two banner petals form a small yellow indentation (color yellow 9B) just above the reproductive organs. Center of two lateral petals form curved nectar spurs.
*Petal margin.*—Entire.
*Petal surface texture.*—Smooth.
*Size of the banner petals.*—Length: 5–7 mm. Width: 5–7 mm.
*Size of the lateral petals.*—Length: 6–8 mm. Width 5–7 mm.
*Size of the basal lip petal.*—Length: 14–16 mm. Width: 12–14 mm.
*Spur.*—Length: 9 mm. Color: 63B.
*Number of flowers per raceme.*—45–65.
*Fragrance.*—No fragrance.
*Lastingness of the bloom.*—New florets continue to open in one raceme over a period of 19 days.
*Lastingness of one flower.*—About 5 days depending on temperature.

The reproductive organs:
*Androecium.*—Stamen number: Three. Anther shape: Two-lobed. Anther size: Less than 1 mm. Anther color: 7C. Amount of pollen: Very much pollen. Pollen color: 7C.
*Gynoecium.*—Pistil number: 1. Stigma shape: Rounded. Pistil length: 2–3 mm. Style color: 144B. Stigma color: 157A. Ovary color: 144A.

The seed:
*Seedset.*—No seedset has been observed.

The roots:
*Type of roots.*—Fibrous.
*Rooting habit.*—Fine and freely branching.

Physiological and ecological characteristics: Good tolerance to heat and cold. Strong resistance to pests and diseases.

What is claimed is:

1. A new and distinct cultivar of Diascia plant named 'Diastara', as substantially illustrated and described herein.

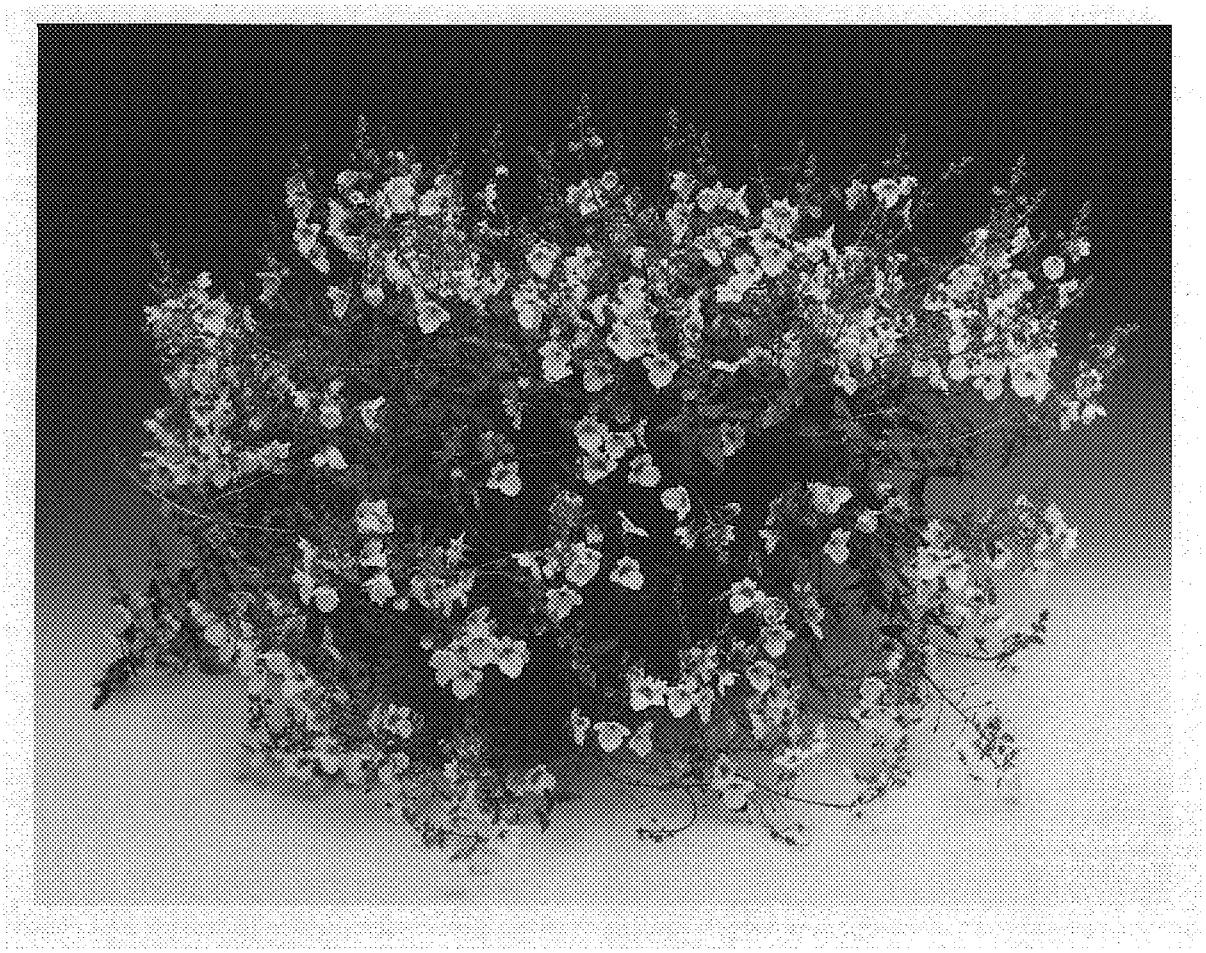

* * * * *